(12) United States Patent
Clark et al.

(10) Patent No.: US 6,712,121 B2
(45) Date of Patent: Mar. 30, 2004

(54) ANTIMICROBIALLY-TREATED FABRICS

(75) Inventors: James W. Clark, Roswell, GA (US); Shawn E. Jenkins, Duluth, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/976,676

(22) Filed: Oct. 12, 2001

(65) Prior Publication Data

US 2003/0127207 A1 Jul. 10, 2003

(51) Int. Cl.⁷ .................. D21H 21/36; A01N 25/32
(52) U.S. Cl. .............. 164/161; 162/158; 162/164.1; 424/402
(58) Field of Search .................. 162/160–161, 162/158, 164.1, 179; 424/402, 403, 409, 411, 414, 416

(56) References Cited

U.S. PATENT DOCUMENTS

| | | |
|---|---|---|
| 2,474,306 A * | 6/1949 | Doub .................. 424/445 |
| 2,666,369 A | 1/1954 | Niks |
| 2,756,647 A * | 7/1956 | Thompson .................. 118/314 |
| 3,338,992 A | 8/1967 | Kinney |
| 3,341,394 A | 9/1967 | Kinney |
| 3,485,706 A | 12/1969 | Evans |
| 3,502,763 A | 3/1970 | Hartman |
| 3,542,615 A | 11/1970 | Dobo et al. |
| 3,692,618 A | 9/1972 | Dorschner et al. |
| 3,719,697 A | 3/1973 | Michael et al. |
| 3,730,701 A | 5/1973 | Isquith et al. |
| 3,802,817 A | 4/1974 | Matsuki et al. |
| 3,821,068 A | 6/1974 | Shaw |
| 3,849,241 A | 11/1974 | Butin et al. |
| 3,855,046 A | 12/1974 | Hansen et al. |
| 4,282,366 A | 8/1981 | Eudy |
| 4,340,563 A | 7/1982 | Appel et al. |
| 4,394,378 A | 7/1983 | Klein |
| 4,395,454 A | 7/1983 | Baldwin |
| 4,401,712 A | 8/1983 | Morrison |
| 4,406,738 A | 9/1983 | Fink et al. |
| 4,406,892 A | 9/1983 | Eudy |
| 4,408,996 A | 10/1983 | Baldwin |
| 4,411,928 A | 10/1983 | Baldwin |
| 4,414,268 A | 11/1983 | Baldwin |
| 4,425,372 A | 1/1984 | Baldwin |
| 4,447,498 A | 5/1984 | Fink |
| 4,467,013 A | 8/1984 | Baldwin |
| 4,504,541 A | 3/1985 | Yasuda et al. |
| 4,533,435 A * | 8/1985 | Intili .................. 162/161 |
| 4,615,937 A | 10/1986 | Bouchette |
| 4,692,374 A | 9/1987 | Bouchette |
| 4,737,405 A | 4/1988 | Bouchette |
| 4,740,398 A | 4/1988 | Bouchette |
| 4,772,492 A | 9/1988 | Bouchette |
| 4,781,974 A | 11/1988 | Bouchette et al. |
| 4,837,079 A | 6/1989 | Quantrille et al. |
| 4,874,662 A | 10/1989 | Huhn |
| 4,929,498 A | 5/1990 | Suskind et al. |
| 5,064,599 A | 11/1991 | Ando et al. |
| 5,091,102 A | 2/1992 | Sheridan |
| 5,098,417 A | 3/1992 | Yamazaki et al. |
| 5,140,561 A * | 8/1992 | Miyashita et al. .......... 340/7.41 |
| 5,169,625 A | 12/1992 | Blank |
| 5,284,703 A | 2/1994 | Everhart et al. |
| 5,350,625 A | 9/1994 | Peterson et al. |
| 5,382,400 A | 1/1995 | Pike et al. |
| 5,389,202 A * | 2/1995 | Everhart et al. ............ 162/103 |
| 5,464,851 A * | 11/1995 | Morpeth .................. 106/124.6 |
| 5,561,167 A | 10/1996 | Matsumoto et al. |
| 5,573,641 A | 11/1996 | Meade et al. |
| 5,620,779 A | 4/1997 | Levy et al. |
| 5,652,049 A | 7/1997 | Suzuki |
| 5,707,736 A | 1/1998 | Levy et al. |
| D390,708 S | 2/1998 | Brown |
| 5,783,502 A | 7/1998 | Swanson |
| 5,786,282 A | 7/1998 | Carter et al. |
| 5,853,859 A | 12/1998 | Levy et al. |
| 5,962,112 A | 10/1999 | Haynes et al. |
| 5,968,539 A | 10/1999 | Beerse et al. |
| 5,985,301 A | 11/1999 | Nakamura et al. |
| 6,080,686 A | 6/2000 | Floyd |
| D428,267 S | 7/2000 | Romano et al. |
| 6,093,665 A | 7/2000 | Sayovitz et al. |
| 6,103,061 A | 8/2000 | Anderson et al. |
| 6,106,851 A | 8/2000 | Beerse et al. |
| 6,113,933 A | 9/2000 | Beerse et al. |
| 6,136,770 A | 10/2000 | Cheung et al. |
| 6,160,196 A | 12/2000 | Knieler et al. |
| 6,183,757 B1 | 2/2001 | Beerse et al. |
| 6,183,763 B1 | 2/2001 | Beerse et al. |
| 6,190,674 B1 | 2/2001 | Beerse et al. |
| 6,190,675 B1 | 2/2001 | Beerse et al. |
| 6,197,315 B1 | 3/2001 | Beerse et al. |

(List continued on next page.)

FOREIGN PATENT DOCUMENTS

WO     WO 0149259 A2     7/2001

OTHER PUBLICATIONS

Int'l Search Report for PCT/US 02/24912 dated Oct. 14, 2002.

*Primary Examiner*—Jose A. Fortuna
(74) *Attorney, Agent, or Firm*—Dority & Manning, P.A.

(57) ABSTRACT

A method for forming an antimicrobially-treated fabric is provided. The method includes forming a solution from a liquid and an antimicrobial agent, such as 3-(trimethoxysilyl)propyloctadecyldimethyl ammonium chloride. In one embodiment, a cellulosic fibrous material is combined with the solution while in the pulper to form a liquid suspension such that the antimicrobial agent becomes substantive to the cellulosic fibrous material. A web is formed from the antimicrobially-treated cellulosic fibrous material such that substantially all of the cellulosic fibrous material present within the web is derived from the antimicrobially-treated cellulosic fibrous material. In one embodiment, the web of antimicrobially-treated fibrous material is also hydraulically entangled with a nonwoven substrate. In some embodiments, when dried, the antimicrobial agent forms a covalent bond with the cellulosic fibrous material.

45 Claims, 3 Drawing Sheets

U.S. PATENT DOCUMENTS

| | | |
|---|---|---|
| 6,197,404 B1 | 3/2001 | Varona |
| 6,210,695 B1 | 4/2001 | Beerse et al. |
| 6,214,363 B1 | 4/2001 | Beerse et al. |
| 6,217,887 B1 | 4/2001 | Beerse et al. |
| 6,228,389 B1 | 5/2001 | McCue et al. |
| 6,258,368 B1 | 7/2001 | Beerse et al. |
| 6,264,936 B1 | 7/2001 | Sawan et al. |
| 6,274,520 B1 | 8/2001 | Cordell |
| 6,284,259 B1 | 9/2001 | Beerse et al. |
| 6,287,577 B1 | 9/2001 | Beerse et al. |

* cited by examiner

ANTIMICROBIALLY-TREATED FABRICS

BACKGROUND OF THE INVENTION

In many different industries, microorganism contamination can be a significant problem. For example, in the food service industry, food products are often prepared on hard surfaces such as counters, tables, and the like. Microbes (e.g., viruses, bacteria, fungi, and the like) from these products can collect on the surfaces, and later transfer to a cleaning cloth, towel, or wipe that is used to clean the surfaces. After transfer, the microbes can remain on the cloth, towel, or wipe and begin to grow in population due to the favorable environment often provided by such materials. Thus, such microbes can actually cross-contaminate other environments, such as additional surfaces, the hands or skin of a user, etc., when contacted therewith.

In an attempt to prevent such surface and cloth contamination, wipers containing certain antimicrobial agents have been employed. For instance, many of these antimicrobial wipers are impregnated with antimicrobial agents that are delivered to the user in a premoistened form. However, the disinfecting agent within the wiper is readily exhausted after a short period of time. Thus, such premoistened wipers either only mildly inhibit growth on the wipers and/or the hard surfaces cleaned or may only be used for a very limited number of wipes.

Other types of wipers have also been developed to provide antimicrobial activity. For example, one such wiper is described in U.S. Pat. No. 4,929,498 to Suskind, et al. In particular, the wiper described in Suskind, et al. is formed from a nonwoven fabric that contains fibers and an antimicrobial agent (preferably an organosilicon quaternary ammonium salt) distributed on 10% through 50% of the fibers. The antimicrobial agent is said to be substantive to the fibers so that it is substantially prevented from diffusing therefrom. However, although such wipers may overcome the problems of conventional premoistened wipers in which the antimicrobial agent is readily exhausted, such wipers still tend to provide inadequate microbial kill percentage.

Another conventional wiper, known as the "Keri Klean" food service wiper, is formed from rayon and polyester fibers in a dry lay carding process. The fibers are then subjected to hydroentanglement and then saturated in a bath that contains an antimicrobial agent. After being applied with the antimicrobial agent, liquid is squeezed from the nonwoven material, which is then dried. However, one problem with such a method is that, in order to "dip and squeeze" the nonwoven into an antimicrobial bath, additional equipment may be required. Such additional equipment can decrease the efficiency of the process, as well as increase costs.

As such, a need currently exists for a more effective method of forming an antimicrobial nonwoven product, such as a cloth, towel, or wipe.

SUMMARY OF THE INVENTION

In accordance with one embodiment of the present invention, a method for forming an antimicrobially-treated fabric is provided that includes forming a solution from a liquid and an antimicrobial agent. In general, any of a variety of antimicrobial agents can be used in the present invention. For example, in some embodiments, the antimicrobial agent is an organosilicone quaternary ammonium compound. One suitable organosilicone quaternary ammonium compound that can be used in the present invention has the following structure:

wherein,
$R_1$ is hydrogen or a $C_1$–$C_8$ alkyl group;
$R_2$ is hydrogen or a $C_1$–$C_8$ alkyl group;
$R_3$ and $R_4$ are the same or different, and are selected from the group consisting of hydrogen and a $C_1$–$C_4$ alkyl group;
$R_5$ is hydrogen or a $C_1$–$C_{30}$ alkyl group; and
$X^-$ is a suitable counterion.

For example, in one embodiment, the antimicrobial agent is 3-(trimethoxysilyl)propyloctadecyidimethyl ammonium chloride.

A cellulosic fibrous material is combined with the solution to form a liquid suspension in which the antimicrobial agent becomes substantive to the cellulosic fibrous material after being combined therewith. The antimicrobial agent can be present within the solution in an amount up to about 5% by weight of the treated fibrous material, in some embodiments between about 0.04% to about 1.0% by weight of the treated fibrous material, and in some embodiments, between about 0.2% to about 0.5% by weight of the treated fibrous material. In some embodiments, the cellulosic fibrous material and antimicrobial solution are combined in a pulper. The materials may also be subjected to agitation, if desired, to improve the likelihood that substantially all of the antimicrobial agent will become substantive to the cellulosic fibrous material.

The liquid suspension is then formed into a web using any of a variety of techniques such that substantially all of the cellulosic fibrous material present within the web is derived from the antimicrobially-treated cellulosic fibrous material. In some embodiments, the web of antimicrobially-treated fibrous material may also be hydraulically entangled with a nonwoven substrate. The nonwoven substrate may be formed from continuous filaments, such as those formed by a spunbond process. In some embodiments, the web of antimicrobially-treated fibrous material is then dried so that the antimicrobial agent forms a covalent bond with the cellulosic fibrous material.

In some embodiments, during formation of the fabric, such as described above, at least a portion of the liquid is removed from the liquid suspension. Such removal can be accomplished in a variety of different ways, such as through the use of gravity, vacuum boxes or shoes, dryers, and the like. However, regardless of the mechanism used to remove the liquid, the portion of the liquid that is removed is substantially free from the antimicrobial agent. Accordingly, such liquid may sometimes be recycled or disposed of without requiring additional mechanical or chemical treatment.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Repeat use of reference characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents.

DEFINITIONS

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns.

As used herein the term "meltblown fibers" means fibers formed by extruding a molten thermoplastic material through a plurality of fine, usually circular, die capillaries as molten threads or filaments into converging high velocity gas (e.g. air) streams that attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonded filaments" refers to small diameter substantially continuous filaments which are formed by extruding a molten thermoplastic material as filaments from a plurality of fine, usually circular, capillaries of a spinnerette with the diameter of the extruded filaments then being rapidly reduced as by, for example, eductive drawing and/or other well-known spunbonding mechanisms. The production of spun-bonded nonwoven webs is illustrated in patents such as, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Levy, U.S. Pat. No. 3,542,615 to Dobo et al., and U.S. Pat. No. 5,382,400 to Pike, et al., which are incorporated herein in their entirety by reference thereto for all purposes. Spunbond filaments are generally not tacky when they are deposited onto a collecting surface. Spunbond filaments can sometimes have diameters less than about 40 microns, and are often between about 5 to about 20 microns.

As used herein, the term "pulp" refers to fibers from natural sources such as woody and non-woody plants. Woody plants include, for example, deciduous and coniferous trees. Non-woody plants include, for example, cotton, flax, esparto grass, milkweed, straw, jute hemp, and bagasse.

As used herein, the term "average fiber length" refers to a weighted average length of pulp fibers determined utilizing a Kajaani fiber analyzer model No. FS-100 available from Kajaani Oy Electronics, Kajaani, Finland. According to the test procedure, a pulp sample is treated with a macerating liquid to ensure that no fiber bundles or shives are present. Each pulp sample is disintegrated into hot water and diluted to an approximately 0.001% solution. Individual test samples are drawn in approximately 50 to 100 ml portions from the dilute solution when tested using the standard Kajaani fiber analysis test procedure. The weighted average fiber length may be expressed by the following equation:

$$\sum_{x_i}^{k} (x_i * n_i)/n$$

wherein,
k=maximum fiber length $x_i$=fiber length
$n_i$=number of fibers having length $x_i$; and
n=total number of fibers measured.

As used herein, the term "low-average fiber length pulp" refers to pulp that contains a significant amount of short fibers and non-fiber particles. Many secondary wood fiber pulps may be considered low average fiber length pulps; however, the quality of the secondary wood fiber pulp will depend on the quality of the recycled fibers and the type and amount of previous processing. Low-average fiber length pulps may have an average fiber length of less than about 1.2 mm as determined by an optical fiber analyzer such as, for example, a Kajaani fiber analyzer model No. FS-100 (Kajaani Oy Electronics, Kajaani, Finland). For example, low average fiber length pulps may have an average fiber length ranging from about 0.7 to 1.2 mm. Exemplary low average fiber length pulps include virgin hardwood pulp, and secondary fiber pulp from sources such as, for example, office waste, newsprint, and paperboard scrap.

As used herein, the term "high-average fiber length pulp" refers to pulp that contains a relatively small amount of short fibers and non-fiber particles. High-average fiber length pulp is typically formed from certain non-secondary (i.e., virgin)

fibers. Secondary fiber pulp that has been screened may also have a high-average fiber length. High-average fiber length pulps typically have an average fiber length of greater than about 1.5 mm as determined by an optical fiber analyzer such as, for example, a Kajaani fiber analyzer model No. FS-100 (Kajaani Oy Electronics, Kajaani, Finland). For example, a high-average fiber length pulp may have an average fiber length from about 1.5 mm to about 6 mm. Exemplary high-average fiber length pulps that are wood fiber pulps include, for example, bleached and unbleached virgin softwood fiber pulps.

As used herein, the phrase "antimicrobial" or "antimicrobial agent" refers to a composition or moiety that can prevent the growth of *Escherichia coli* (ATCC #11229), *Staphylococcus aureus* (ATCC #6538) (both bacteria), and/or *Candida albicans* (ATCC #10231) (yeast). For example, in some embodiments, kill rates of the above-mentioned microbes can be determined according to ASTM No. E2149-01, which is entitled "Determining the Antimicrobial Activity of Immobilized Antimicrobial Agents Under Dynamic Contact Conditions".

DETAILED DESCRIPTION

The present invention is generally directed to a method for forming an antimicrobially-treated fabric in which the antimicrobial agent becomes substantive to the cellulosic fibrous material during the papermaking process. For example, in one embodiment, an organosilicone quaternary ammonium compound is initially applied to a pulper containing a liquid (e.g., water). Thereafter, a cellulosic fibrous material is applied to the pulper and mixed under agitation with the antimicrobially-treated water. It is believed that, due to the partial negative charge present on the cellulosic fibers, the cationic quaternary ammonium group of the organosilicone quaternary ammonium antimicrobial agent can form an associative bond with the pulp fibers. In addition, once associatively bonded to the antimicrobial agent, the fibrous material can then be formed into a cellulosic web. When dried, the antimicrobial agent is cured, thereby forming a covalent bond with the cellulosic fibers. Surprisingly, it has been discovered that any water removed during the papermaking process can be substantially free from any residual antimicrobial agent, thereby allowing it to be recycled or disposed of without any additional mechanical or chemical treatments.

In general, any of a variety of antimicrobial agents that are capable of becoming substantive to a cellulosic fibrous material can be used in the present invention. For example, in some embodiments, the antimicrobial agent can be an organosilicone compound. Some examples of organosilicone compounds that are believed to be suitable for use in the present invention include, but are not limited to, organosilicone derivatives of the following ammonium salts: di-isobutylcresoxyethoxyethyl dimethyl benzyl ammonium chloride, di-isobutylphenoxyethoxyethyl dimethyl benzyl ammonium chloride, myristyl dimethylbenzyl ammonium chloride, myristyl picolinium chloride, N-ethyl morpholinium chloride, laurylisoquinolinium bromide, alkyl imidazolinium chloride, benzalkonium chloride, cetyl pyridinium chloride, coconut dimethyl benzyl ammonium chloride, stearyl dimethyl benzyl ammonium chloride, alkyl dimethyl benzyl ammonium chloride, alkyl diethyl benzyl ammonium chloride, alkyl dimethyl benzyl ammonium bromide, di-isobutyl phenoxyethoxyethyl trimethyl ammonium chloride, di-isobutylphenoxyethoxyethyl dimethyl alkyl ammonium chloride, methyl-dodecylbenzyl trimethyl ammonium chloride, cetyl trimethyl ammonium bromide, octadecyl dimethyl ethyl ammonium bromide, cetyl dimethyl ethyl ammonium bromide, octadec-9-enyl dimethyl ethyl ammonium bromide, dioctyl dimethyl ammonium chloride, dodecyl trimethyl ammonium chloride, octadecyl trimethyl ammonium chloride, octadecyl trimethyl ammonium bromide, hexadecyl trimethyl ammonium iodide, octyl trimethyl ammonium fluoride, and mixtures thereof. Other examples of suitable organosilicone compounds may be described in U.S. Pat. No. 3,719,697 to Michael, et al.; U.S. Pat. No. 3,730,701 to Isquith, et al.; U.S. Pat. No. 4,395,454 to Klein; U.S. Pat. No. 4,615,937 to Bouchette; and U.S. Pat. No. 6,136,770 to Cheung, et al., which are incorporated herein in their entirety by reference thereto for all purposes.

One particular example of a suitable organosilicone compound is a silane quaternary ammonium compound having the following structure:

wherein, $R_1$ is hydrogen or a $C_1$–$C_8$ alkyl group (e.g., $CH_3$);

$R_2$ is hydrogen or a $C_1$–$C_8$ alkyl group;

$R_3$ and $R_4$ can be the same or different, and can be selected from the group consisting of hydrogen and a $C_1$–$C_4$ alkyl group (e.g., $CH_3$);

$R_5$ is hydrogen or a $C_1$–$C_{30}$ alkyl group (e.g., $C_{18}H_{37}$); and $X^-$ is a suitable counterion, such as a halogen ion (e.g., $Cl^-$ or $Br^-$).

A commercially available example of such a silane quaternary ammonium compound is AEM 5772, which can be obtained from Aegis Environments Co., Midland, Mich. In particular, AEM 5772 contains 3-(trimethoxysilyl) propyloctadecyldimethyl ammonium chloride, which has the following chemical structure:

The quaternary compound in AEM 5772, is contained in a water/methanol mixture in an amount of 72% by weight of the solution.

In accordance with the present invention, an antimicrobial agent, such as described above, can generally be combined with the cellulosic fibrous material at a variety of different stages of a papermaking process. Typically, the antimicrobial agent is added during the preparation of the fibrous slurry used to form the web. For example, referring to FIG. 1, one embodiment of a process for treating cellulosic fibers with an antimicrobial agent is shown. Specifically, a conventional papermaking fiber stock prep beater or pulper 13 is initially provided with a liquid (usually water). Thereafter, an antimicrobial agent is applied to the pulper 13. In some embodiments, the antimicrobial agent may be hydrolyzed by the water in the pulper 13. For example, in one embodiment, 3-(trimethoxysilyl) propyloctadecyidimethyl ammonium chloride is hydrolyzed by the water within the pulper 13. However, it should be understood that the antimicrobial agent can also be hydrolyzed prior to addition to the pulper 13. Moreover, in some instances, the antimicrobial agent may require no hydrolyzation at all.

Figure 1:
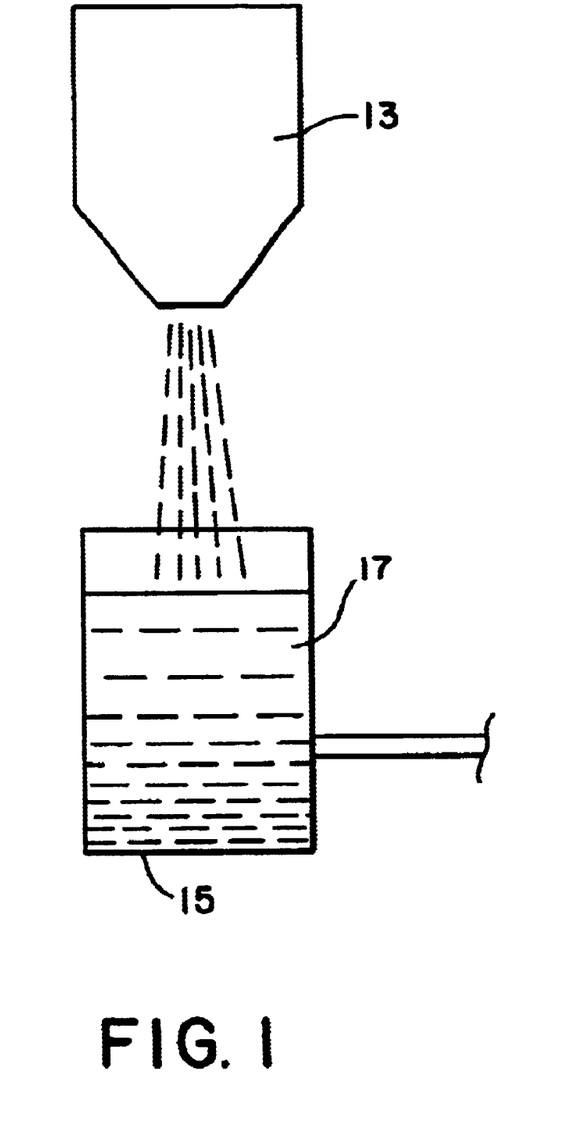
FIG. 1 is a schematic illustration of a process for incorporating an antimicrobial agent into the pulper of a papermaking process.

The amount of antimicrobial agent added to the pulper 13 can generally vary as desired. For example, in some embodiments, the antimicrobial agent may be added to the pulper 13 in an amount up to about 5% by weight of the treated fibrous material, in some embodiments between about 0.04% to about 1.0% by weight of the treated fibrous material, and in some embodiments, between about 0.2% to about 0.5% by weight of the treated fibrous material.

Once optionally hydrolyzed, a cellulosic fibrous material may then be applied to the pulper 13. Any of a variety of cellulosic fibrous materials may generally be utilized in the present invention. For instance, the cellulosic fibrous material can include pulp fibers, synthetic cellulosic fibers, modified cellulosic fibers, combinations thereof, and the like. Some examples of suitable cellulosic fiber sources include virgin wood fibers, such as thermomechanical, bleached and unbleached softwood and hardwood pulps. Secondary or recycled fibers, such as obtained from office waste, newsprint, brown paper stock, paperboard scrap, etc., may also be used. Further, vegetable fibers, such as abaca, flax, milkweed, cotton, modified cotton, cotton linters, can also be used. In addition, synthetic cellulosic fibers such as, for example, rayon and viscose rayon may be used. Modified cellulosic fibers may also be used. For example, the fibrous material may be composed of derivatives of cellulose formed by substitution of appropriate radicals (e.g., carboxyl, alkyl, acetate, nitrate, etc.) for hydroxyl groups along the carbon chain. These fibers may be used alone, in combination with other cellulosic fibers and/or non-cellulosic fibers. Particulates and/or other materials may also be used with the fibrous materials.

When utilized, pulp fibers may have any high-average fiber length pulp, low-average fiber length pulp, or mixtures of the same. High-average fiber length pulp fibers typically have an average fiber length from about 1.5 mm to about 6 mm. Some examples of such fibers may include, but are not limited to, northern softwood, southern softwood, redwood, red cedar, hemlock, pine (e.g., southern pines), spruce (e.g., black spruce), combinations thereof, and the like. Exemplary high-average fiber length wood pulps include those available from the Kimberly-Clark Corporation under the trade designation "Longlac 19".

The low-average fiber length pulp may be, for example, certain virgin hardwood pulps and secondary (i.e. recycled) fiber pulp from sources such as, for example, newsprint, reclaimed paperboard, and office waste. Hardwood fibers, such as eucalyptus, maple, birch, aspen, and the like, can also be used. Low-average fiber length pulp fibers typically have an average fiber length of less than about 1.2 mm, for example, from 0.7 mm to 1.2 mm. Mixtures of high-average fiber length and low-average fiber length pulps may contain a significant proportion of low-average fiber length pulps. For example, mixtures may contain more than about 50 percent by weight low-average fiber length pulp and less than about 50 percent by weight high-average fiber length pulp. One exemplary mixture contains 75 percent by weight low-average fiber length pulp and about 25 percent high-average fiber length pulp.

Once supplied to the pulper 13, the fibrous slurry may be kept in continuous agitation to form a liquid suspension. Although not required, such continuous agitation can ensure that the liquid suspension of fibrous material and antimicrobial agent are well mixed, thus enhancing the uniformity of the distribution of the antimicrobial agent throughout the fibrous slurry. However, it should be understood that, if desired, agitation may be stopped or used intermittently if excessive agitation would be harmful to the antimicrobial agent or fibrous material.

While present within the pulper 13, the antimicrobial agent can become substantive to the cellulosic fibrous material. Specifically, partially charged groups present on cellulosic fibers (e.g., hydroxy moieties) can form associative bonds with the positively charged quaternary ammonium portion of the antimicrobial agent. Moreover, when subjected to continuous agitation, such as described above, a greater likelihood exists that the antimicrobial agent will be brought into contact with any free partially charged groups on the cellulosic fibers. Thus, substantially all of the antimicrobial agent present within the pulper 13 can become associatively bonded to the fibrous material. As such, any liquid that is later removed during the papermaking process, such as through gravity, vacuum boxes or shoes, dryer, and the like, can be substantially free of the antimicrobial agent so that it can be recycled or disposed of without requiring the use of any mechanical or chemical treatments.

After the antimicrobial agent is mixed with the fibrous material within the pulper 13, the resulting fibrous slurry 17 can optionally be diluted and readied for formation into a layer of fibrous material or cellulosic web utilizing conventional wet-laying or papermaking techniques. If desired, the fibrous slurry 17 may be stored in a machine chest 15 prior to web forming. Moreover, the pH of the fibrous slurry 17 may be adjusted if desired for equipment compatibility. It should be understood that, although the antimicrobial agent and fibrous material are described as being admixed in the pulper 13 in the embodiment below, such materials may also be mixed at any stage during the papermaking process occurring prior to or during formation of a cellulosic web. For example, in one embodiment, the antimicrobial agent and fibrous material may be mixed together in the machine chest 15.

Other additives may also be added at the pulper 13, machine chest 15, or immediately prior to forming. Such additives may be added to improve fastness and other properties such as softness and wet-strength. For example, in some embodiments, small amounts of wet-strength resins and/or resin binders may be added to improve strength and abrasion resistance. Useful binders and wet-strength resins include, for example, Kymene 557 H available from the Hercules Chemical Company and Parez 631 available from American Cyanamid, Inc. Cross-linking agents and/or hydrating agents may also be added to the pulp mixture. Debonding agents may be added to the pulp mixture to reduce the degree of hydrogen bonding if a very open or loose nonwoven pulp fiber web is desired. One exemplary debonding agent is available from the Quaker Chemical Company, Conshohocken, Pa., under the trade designation Quaker 2008. The addition of certain debonding agents in the amount of, for example, 1 to 4 percent, by weight, of the composite also appears to reduce the measured static and dynamic coefficients of friction and improve the abrasion resistance of the continuous filament rich side of the composite fabric.

Figure 2:
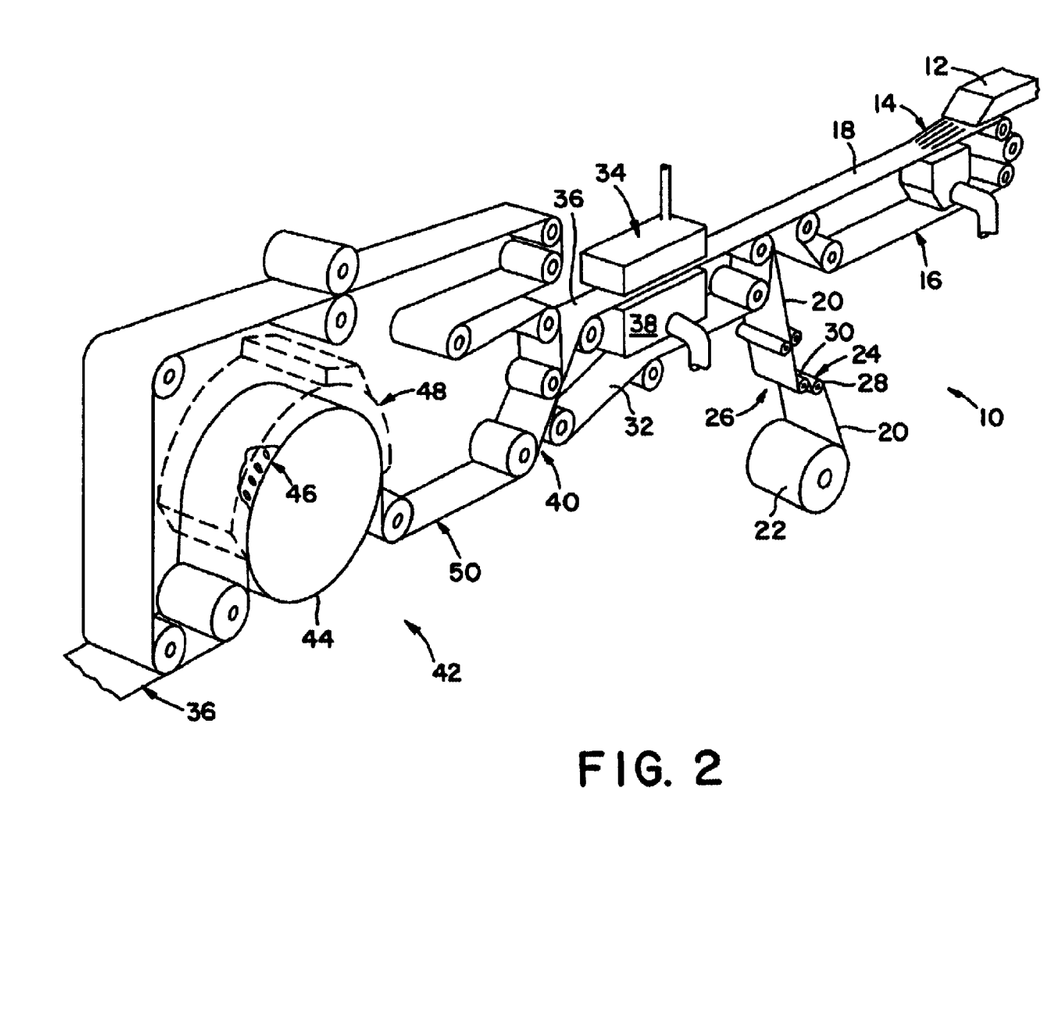
FIG. 2 is a schematic illustration of a process for forming a hydraulically entangled web in accordance with one embodiment of the present invention.

Referring to FIGS. 1–2, the fibrous slurry 17 is then conveyed from the machine chest 15 to a conventional papermaking headbox 12 where it is deposited via a sluice 14 onto a conventional forming fabric or surface 16. The suspension of treated cellulosic fibrous material may have any consistency that is typically used in conventional papermaking processes. For example, the suspension may contain from about 0.01 to about 1.5 percent by weight treated cellulosic fibrous material suspended in water. Water is then removed from the suspension of treated cellulosic fibrous material to form a uniform layer of cellulosic fibrous material 18.

A nonwoven substrate 20 is also unwound from a supply roll 22 and travels in the direction indicated by the arrow associated therewith as the supply roll 22 rotates in the direction of the arrows associated therewith. The nonwoven substrate 20 passes through a nip 24 of a S-roll arrangement 26 formed by the stack rollers 28 and 30.

The nonwoven substrate 20 may be formed by a variety of different processes and from a variety of different materials. For instance, the nonwoven substrate 20 can be formed from continuous filaments, staple fibers, and the like. Continuous filaments, for example, can be produced by known continuous filament nonwoven extrusion processes, such as, for example, known solvent spinning or melt-spinning processes, and passed directly through the nip 16 without first being stored on a supply roll. In one embodiment, the nonwoven substrate 20 is a nonwoven web of continuous melt-spun filaments formed by a spunbond process. The spunbond filaments may be formed from any melt-spinnable polymer, co-polymers or blends thereof. For example, the spunbond filaments may be formed from polyolefins, polyamides, polyesters, polyurethanes, A-B and A-B-A' block copolymers where A and A' are thermoplastic endblocks and B is an elastomeric midblock, and copolymers of ethylene and at least one vinyl monomer such as, for example, vinyl acetates, unsaturated aliphatic monocarboxylic acids, and esters of such monocarboxylic acids. If the filaments are formed from a polyolefin such as, for example, polypropylene, the nonwoven substrate 20 may have a basis weight from about 3.5 to about 150 grams per square meter (gsm), in some embodiments, between about 5 to about 70 gsm, and in some embodiments, between about 10 to about 35 gsm. The polymers may include additional materials such as, for example, pigments, antioxidants, flow promoters, stabilizers and the like.

The nonwoven substrate 20 may be bonded to improve the durability, strength, hand, aesthetics and/or other properties of the substrate 20. By way of example only, the nonwoven substrate 20 can be thermally, ultrasonically, adhesively and/or mechanically bonded. The nonwoven substrate 20 is desirably pattern bonded. As an example, the nonwoven substrate 20 can be point bonded to provide a fabric having numerous small, discrete bond points. An exemplary bonding process is thermal point bonding and this process generally involves passing one or more layers to be bonded between heated rolls such as, for example an engraved patterned roll and a second bonding roll. The engraved roll is patterned in some way so that the fabric is not bonded over its entire surface, and the second roll can be smooth or patterned. As a result, various patterns for engraved rolls have been developed for functional as well as aesthetic reasons. Exemplary bond patterns include, but are not limited to, those described in U.S. Pat. No. 3,855,046 to Hansen et al., U.S. Pat. No. 5,620,779 to Levy et al., U.S. Pat. No. 5,962,112 to Haynes et al., U.S. Pat. 6,093,665 to Sayovitz et al., U.S. Design Pat. No. 428,267 to Romano et al. and U.S. Design Pat. No. 390,708 to Brown, which are incorporated herein in their entirety by reference thereto for all purposes. For instance, in some embodiments, the nonwoven substrate 20 may be optionally bonded to have a total bond area of less than about 30 percent and a uniform bond density greater than about 100 bonds per square inch. For example, the nonwoven substrate 20 may have a total bond area from about 2 to about 30 percent (as determined by conventional optical microscopic methods) and a bond density from about 250 to about 500 pin bonds per square inch. Such a combination of total bond area and bond density may, in some embodiments, be achieved by bonding the nonwoven substrate 20 with a pin bond pattern having more than about 100 pin bonds per square inch that provides a total bond surface area less than about 30 percent when fully contacting a smooth anvil roll. In some embodiments, the bond pattern may have a pin bond density from about 250 to about 350 pin bonds per square inch and a total bond surface area from about 10 percent to about 25 percent when contacting a smooth anvil roll.

Further, the nonwoven substrate 20 can be bonded by continuous seams or patterns. As additional examples, the nonwoven substrate 20 can be bonded along the periphery of the sheet or simply across the width or cross-direction (CD) of the fabric adjacent the edges. Other bond techniques, such as a combination of thermal bonding and latex impregnation, may also be used. Alternatively and/or additionally, a resin, latex or adhesive may be applied to the nonwoven substrate 20 by, for example, spraying or printing, and dried to provide the desired bonding. Still other suitable bonding techniques may be described in U.S. Pat. No. 5,284,703 to Everhart, et al., U.S. Pat. No. 6,103,061 to Anderson, et al., and U.S. Pat. No. 6,197,404 to Varona, which are incorporated herein in its entirety by reference thereto for all purposes.

The treated cellulosic fibrous layer 18 is then laid on the nonwoven substrate 20 that rests upon a foraminous entangling surface 32 of a conventional hydraulic entangling machine. Although not required, it is typically desired that the treated cellulosic fibrous layer 18 be between the nonwoven substrate 20 and the hydraulic entangling manifolds 34. The treated cellulosic fibrous layer 18 and nonwoven substrate 20 pass under one or more hydraulic entangling manifolds 34 and are treated with jets of fluid to entangle the treated cellulosic fibrous material with the filaments of the continuous filament nonwoven substrate 20. The jets of fluid also drive cellulosic fibers into and through the nonwoven substrate 20 to form the composite material 36.

Alternatively, hydraulic entangling may take place while the treated cellulosic fibrous layer 18 and nonwoven substrate 20 are on the same foraminous screen (i.e., mesh fabric) that the wet-laying took place. The present invention also contemplates superposing a dried cellulosic fibrous sheet on a continuous filament nonwoven substrate, rehydrating the dried sheet to a specified consistency and then subjecting the rehydrated sheet to hydraulic entangling.

The hydraulic entangling may take place while the treated cellulosic fibrous layer 18 is highly saturated with water. For example, the treated cellulosic fibrous layer 18 may contain up to about 90 percent by weight water just before hydraulic entangling. Alternatively, the treated cellulosic fibrous layer may be an air-laid or dry-laid layer.

Hydraulic entangling the wet-laid layer of treated cellulosic fibrous material is desirable because the cellulosic fibers can be embedded into and/or entwined and tangled with the continuous filament substrate without interfering with "paper" bonding (sometimes referred to as hydrogen bonding). "Paper" bonding also appears to improve the abrasion resistance and tensile properties of a high pulp content composite fabric.

The hydraulic entangling may be accomplished utilizing conventional hydraulic entangling equipment such as may be described in, for example, in U.S. Pat. No. 3,485,706 to Evans, which is incorporated herein in its entirety by reference thereto for all purposes. The hydraulic entangling may be carried out with any appropriate working fluid such as, for example, water. The working fluid flows through a manifold that evenly distributes the fluid to a series of individual holes or orifices. These holes or orifices may be from about 0.003 to about 0.015 inch in diameter. For example, a manifold produced by Honeycomb Systems Incorporated of Biddeford, Me., containing a strip having 0.007-inch diameter orifices, 30 holes per inch, and 1 row of holes may be utilized. However, it should also be understood that many other manifold configurations and combinations may be used. For example, a single manifold may be used or several manifolds may be arranged in succession.

In the hydraulic entangling process, the working fluid passes through the orifices at a pressures that typically range from about 200 to about 2000 pounds per square inch gauge (psig). In some embodiments, when processed at the upper ranges of the described pressures, the composite fabrics may be processed at speeds of about 1000 feet per minute (fpm). The fluid impacts the cellulosic fibrous layer 18 and the nonwoven substrate 20 that are supported by a foraminous surface that may be, for example, a single plane mesh having a mesh size of from about 40×40 to about 100×100. The foraminous surface may also be a multi-ply mesh having a mesh size from about 50×50 to about 200×200. As is typical in many water jet treatment processes, vacuum slots 38 may be located directly beneath the hydro-needling manifolds or beneath the foraminous entangling surface 32 downstream of the entangling manifold so that excess water is withdrawn from the hydraulically entangled composite material 36.

Figure 3:
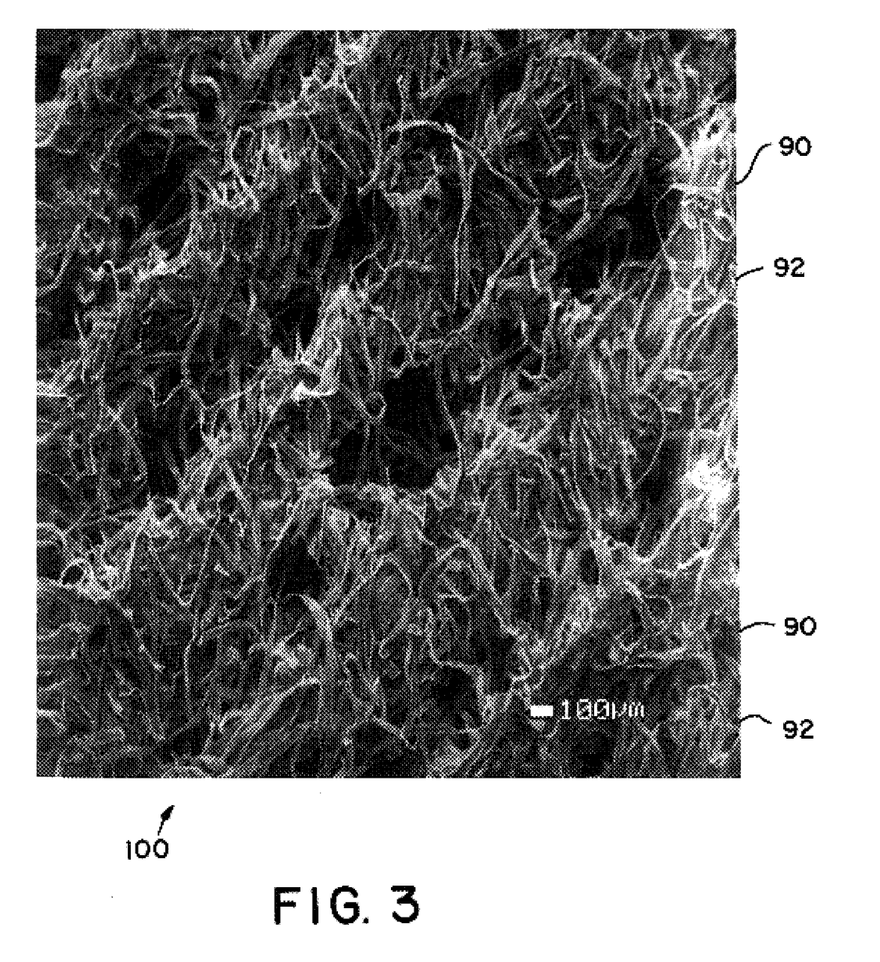
FIG. 3 is an SEM photograph (magnification of 80×) of a cross section of a composite fabric formed according to one embodiment of the present invention.

Although not held to any particular theory of operation, it is believed that the columnar jets of working fluid that directly impact cellulosic fibers laying on the nonwoven substrate work to drive those fibers into and partially through the matrix or nonwoven network of filaments in the substrate. When the fluid jets and cellulosic fibers interact with a nonwoven substrate, the cellulosic fibers are also entangled with filaments of the nonwoven substrate and with each other. Besides causing the fibers to entangle with each other, hydraulically entangling also forms furrows or rows in the material, which may sometimes be desirable for aesthetic and/or other purposes. For example, as shown in FIG. 3, a hydraulically entangled composite material 100 includes furrows or rows 90 defined by entangled fibers 92.

If desired, the energy of the fluid jets that impact the cellulosic fibrous layer 18 and the substrate 20 may be adjusted so that the cellulosic fibers are inserted into and entangled with the continuous filament substrate 20 in a manner that enhances the two-sidedness of the fabric. That is, the entangling may be adjusted to produce a high cellulosic fiber concentration on one side of the fabric and a corresponding low cellulosic fiber concentration on the opposite side. Such a configuration may be particularly useful for special purpose wipers and for personal care product applications such as, for example, disposable diapers, feminine pads, adult incontinence products and the like. Alternatively, the substrate 20 may be entangled with a cellulosic fibrous layer on one side and a different cellulosic fibrous layer on the other side to form a fabric with two cellulosic-rich sides. In such a case, hydraulically entangling both sides of the composite fabric may be desirable.

In accordance with the present invention, it has been surprisingly discovered that the associative bonds formed between the antimicrobial agent and the pulp fibers during stock preparation are not substantially broken by the mechanical forces of the hydraulic entangling process. In particular, it is believed that, when subjected to entangling conditions, such as described above, the associative bond between the quaternary ammonium portion of the antimicrobial agent and the partially charged hydroxy groups of the pulp fibers is strong enough to remain in tact after being hydraulically entangled. Although not limited in theory, it is believed that, in some embodiments, this result is at least partially due to the admixture of the fibers with the antimicrobial agent while under continuous agitation. Specifically, as described above, agitation may allow the untreated fibers to be brought into contact with any unused antimicrobial agent. As a result, substantially all of the antimicrobial agent is able to bond to the fibers, thereby enhancing the durability of the treatment, even when subjected to relatively strong mechanical forces during entanglement.

After the fluid jet treatment, the composite fabric 36 may then be transferred to a non-compressive drying operation. A differential speed pickup roll 40 may be used to transfer the material from the hydraulic needling belt to a non-compressive drying operation. Alternatively, conventional vacuum-type pickups and transfer fabrics may be used. If desired, the composite fabric may be wet-creped before being transferred to the drying operation. Non-compressive drying of the web may be accomplished utilizing a conventional rotary drum through-air drying apparatus 42. The through-dryer 42 may be an outer rotatable cylinder 44 with perforations 46 in combination with an outer hood 48 for receiving hot air blown through the perforations 46. A through-dryer belt 50 carries the composite fabric 36 over the upper portion of the through-dryer outer cylinder 40. The heated air forced through the perforations 46 in the outer cylinder 44 of the through-dryer 42 removes water from the composite fabric 36. The temperature of the air forced through the composite fabric 36 by the through-dryer 42 may range from about 200° F. to about 500° F. Other useful through-drying methods and apparatus may be found in, for example, U.S. Pat. Nos. 2,666,369 to Niks and 3,821,068 to Shaw, which are incorporated herein in their entirety by reference thereto for all purposes.

When dried, such as described above, the antimicrobial agent becomes covalently bonded to the cellulosic fibers. For example, in one embodiment, the organosilicone antimicrobial compound is believed to form a siloxane bond (i.e., O—Si—O) with free hydroxy groups of the cellulosic fibers. By forming such a covalent bond with the cellulosic fibers, the durability of the antimicrobial treatment can be significantly enhanced to provide antimicrobial activity to the fabric for an extended period of time.

It may also be desirable to use finishing steps and/or post treatment processes to impart selected properties to the composite fabric 36. For example, the fabric may be lightly pressed by calender rolls, creped, brushed or otherwise treated to enhance stretch and/or to provide a uniform exterior appearance and/or certain tactile properties. Alternatively or additionally, various chemical post-treatments such as, adhesives or dyes may be added to the fabric. Additional post-treatments that can be utilized are described in U.S. Pat. No. 5,853,859 to Levy, et al., which is incorporated herein in its entirety by reference thereto for all purposes.

The resulting composite fabric 36 can generally have any desired content of antimicrobially-treated cellulosic fibers. For example, in some embodiments, the antimicrobially-treated cellulosic fibers can comprise greater than about 50% by weight of the fabric 36, and in some embodiments, between about 60% to about 90% by weight of the fabric 36. Generally speaking, substantially all of the cellulosic fibers used to form the fabric 36 are antimicrobially-treated. For example, in some embodiments, greater than about 90% of the cellulosic fibers used to form the fabric 36 are antimicrobially-treated. Moreover, depending on the desired antimicrobial activity, the fabric 36 can also contain various levels of the antimicrobial agent. For instance, in some embodiments, the fabric 36 can contain an antimicrobial agent in an amount up to about 4% by weight of the fabric, in some embodiments between about 0.03% to about 0.8% by weight of the fabric, and in some embodiments, between about 0.16% to about 0.4% by weight of the fabric.

The present invention may be better understood with reference to the following examples.

EXAMPLE 1

The ability to form a fabric with antimicrobially-treated cellulosic fibers was demonstrated. Specifically, six samples were produced by initially adding varying amounts of AEM 5772 (See Table I) to 1260 pounds of tap water contained within a pulper. While under continuous agitation, 15 pounds of a pulp mixture (50% by weight northern softwood kraft fibers and 50% by weight southern softwood kraft fibers) were then added to the pulper so that each resulting slurry had a 1.19% solids consistency. The slurry was mixed for 10 minutes and supplied to a dilution tank where it was diluted with tap water to a 0.1% solids consistency.

The resulting slurries were then used to form composite fabrics according to U.S. Pat. No. 5,204,703 to Everhart, et al. Specifically, the treated pulp fibers were hydraulically entangled with a polypropylene spunbond web (basis weight of 27 grams per square meter) with entangling pressures of up to about 1800 pounds per square inch. The entangled fabric was then dried for 1 minute with a through-air dryer (air at a temperature of 450° F.) so that the fabric reached a maximum temperature of 200° F. The resulting fabric had a basis weight of 125 grams per square meter.

Once formed, the antimicrobial activity of each fabric sample was then determined according to ASTM No. E2149-01, which is entitled "Determining the Antimicrobial Activity of Immobilized Antimicrobial Agents Under Dynamic Contact Conditions". The properties of the samples are set forth below in Table I.

TABLE I

Properties of the Samples

| Sample | AEM 5772 Added (72% solids) (grams) | AEM 5772 Pulp Add-On ([wt. AEM solids / wt. of pulp] × 100%) | AEM 5772 Fabric Add-On ([wt. of AEM solids / fabric wt.] × 100%) | Bacterial Reduction (%) |
|---|---|---|---|---|
| 1 | 0.0 | 0.00 | 0.000 | 0 |
| 2 | 54.5 | 0.58 | 0.450 | >97 |
| 3 | 27.2 | 0.29 | 0.230 | >97 |
| 4 | 13.6 | 0.14 | 0.110 | 97 |
| 5 | 6.8 | 0.07 | 0.055 | 89 |
| 6 | 3.4 | 0.04 | 0.031 | 81 |

Thus, as indicated by the results set forth in Table I, a fabric can be provided with a relatively high bacterial kill, such as greater than 97%.

In addition, to determine the amount of the AEM 5772 depleted from water-pulp slurry during pulping, samples of the AEM 5772 treated pulp slurry were taken from the pulper, machine chest, headbox, and post-entangling white water silo. The pulp slurries were de-watered and the captured water samples were each tested with an active quaternary titration using sodium lauryl sulfate, chloroform, a dye, and a buffer. No AEM 5772 silicone quaternary was detected in any of the collected water.

EXAMPLE 2

The ability to form a fabric with antimicrobially-treated cellulosic fibers was demonstrated. Specifically, two samples were produced by initially adding AEM 5772 (See Table II) to 30,000 pounds of mill water contained within a pulper. Prior to being applied to the pulper, the AEM 772 was diluted with water to a 2% solids level.

While under continuous agitation, 2000 pounds of a pulp mixture 50% by weight northern softwood kraft fibers and 50% by weight southern softwood kraft fibers) were then added to the pulper so that each resulting slurry had a 6% solids consistency. The slurries were mixed for 10 minutes and supplied to a dilution tank where they were diluted with tap water to a 2.5% solids consistency.

The resulting slurries were then used to form composite fabrics according to U.S. Pat. No. 5,204,703 to Everhart, et al. The samples were formed in an identical manner, except that Sample 1 was not creped, while Sample 2 was creped. For example, during processing, the treated pulp fibers of each sample were initially diluted to a 0.3% solids consistency. The treated pulp fibers were hydraulically entangled with a polypropylene spunbond web (basis weight of 27 grams per square meter) with entangling pressures of up to about 1800 pounds per square inch. The entangled fabric was then dried with drying cans (at a temperature of 250° F.) so that it reached a maximum temperature of 200° F. The resulting fabric had a basis weight of 125 grams per square meter.

Once formed, the antimicrobial activity of each fabric sample was then determined according to ASTM No. E2149-01, which is entitled "Determining the Antimicrobial Activity of Immobilized Antimicrobial Agents Under Dynamic Contact Conditions". The properties of the samples are set forth below in Table II.

TABLE II

Properties of the Samples

| Sample | AEM 5772 Added (72% solids) (pounds) | AEM 5772 Pulp Add-On ([wt. AEM solids / wt. of pulp] × 100%) | AEM 5772 Fabric Add-On ([wt. of AEM solids / fabric wt.] × 100%) | Bacterial Reduction (%) | Creping |
|---|---|---|---|---|---|
| 1 | 8.3 | 0.30 | 0.23 | >97 | No |
| 2 | 8.3 | 0.30 | 0.23 | >97 | Yes |

Thus, as indicated by the results set forth in Table II, a fabric can be provided with a relatively high bacterial kill, such as greater than 97%.

In addition, to determine the amount of the AEM 5772 depleted from water-pulp slurry during pulping, samples of the AEM 5772 treated pulp slurry were taken from the pulper, machine chest, headbox, and post entangling white water silo. The pulp slurries were de-watered and the captured water samples were each tested with an active quaternary titration using sodium lauryl sulfate, chloroform, a dye, and a buffer. No AEM 5772 silicone quaternary was detected in any of the collected water.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for forming an antimicrobially-treated fabric, said method comprising:
forming a solution from a liquid and an antimicrobial agent, said antimicrobial agent being an organosilicone quaternary ammonium compound;
combining pulp fibers with said solution to form a liquid suspension while under agitation, wherein said organosilicone quaternary ammonium compound becomes substantive to said pulp fibers after being combined therewith;
forming a web from said liquid suspension of said antimicrobially-treated cellulosic fibrous material such that substantially all of the cellulosic fibrous material present within said web is derived from said antimicrobially-treated cellulosic fibrous material
hydraulically entangling said web of antimicrobially-treated pulp fibers with a nonwoven substrate; and
drying said web so that said antimicrobial agent forms a covalent bond with pulp fibers, wherein said antimicrobially-treated cellulosic fibrous material comprises from about 60% to about 90% by weight of the fabric.

2. A method as defined in claim 1, wherein said covalent bond is a siloxane bond.

3. A method as defined in claim 1, wherein at least a portion of said liquid from said liquid suspension is removed during formation of said web, said removed liquid portion being substantially free from said antimicrobial agent.

4. A method as defined in claim 1, wherein said organosilicone quaternary ammonium compound has the following structure:

wherein,
$R_1$ is hydrogen or a $C_1$–$C_8$ alkyl group;
$R_2$ is hydrogen or a $C_1$–$C_8$ alkyl group;
$R_3$ and $R_4$ are the same or different, and are selected from the group consisting of hydrogen and a $C_1$–$C_4$ alkyl group;
$R_5$ is hydrogen or a $C_1$–$C_{30}$ alkyl group; and
$X^-$ is a suitable counterion.

5. A method as defined in claim 1, wherein said antimicrobial agent is 3-(trimethoxysilyl)propyloctadecyldimethyl ammonium chloride.

6. A method as defined in claim 1, wherein said solution and said pulp fibers are combined in a pulper.

7. A method as defined in claim 1, wherein said nonwoven substrate is formed from continuous filaments.

8. A method as defined in claim 7, wherein said continuous filaments are formed by a spunbond process.

9. A method as defined in claim 1, wherein greater than about 90% of the cellulosic fibrous material present within said web is derived from said antimicrobially-treated cellulosic fibrous material.

10. A method for forming an antimicrobially-treated fabric, said method comprising:
forming a solution from a liquid and an antimicrobial agent;
combining a cellulosic fibrous material with said solution to form a liquid suspension, wherein said antimicrobial agent becomes substantive to said cellulosic fibrous material after being combined therewith; and
forming a web from said liquid suspension of said antimicrobially-treated cellulosic fibrous material such that substantially all of the cellulosic fibrous material present within said web is derived from said antimicrobially-treated cellulosic fibrous material; and
hydraulically entangling said web of antimicrobially-treated pulp fibers with a nonwoven substrate, wherein said antimicrobially-treated cellulosic fibrous material comprises from about 60% to about 90% by weight of the fabric.

11. A method as defined in claim 10, wherein at least a portion of said liquid from said liquid suspension is removed during formation of said web, said removed liquid portion being substantially free from said antimicrobial agent.

12. A method as defined in claim 10, wherein said antimicrobial agent is an organosilicone quaternary ammonium compound.

13. A method as defined in claim 12, wherein said organosilicone quaternary ammonium compound has the following structure:

wherein,
$R_1$ is hydrogen or a $C_1$–$C_8$ alkyl group;
$R_2$ is hydrogen or a $C_1$–$C_8$ alkyl group;
$R_3$ and $R_4$ are the same or different, and are selected from the group consisting of hydrogen and a $C_1$–$C_4$ alkyl group;
$R_5$ is hydrogen or a $C_1$–$C_{30}$ alkyl group; and
$X^-$ is a suitable counterion.

14. A method as defined in claim 10, wherein said antimicrobial agent is 3-(trimethoxysilyl) propyloctadecyldimethyl ammonium chloride.

15. A method as defined in claim 10, wherein said antimicrobial agent is hydrolyzed prior to forming said solution.

16. A method as defined in claim 10, wherein said solution and said cellulosic fibrous material are combined in a pulper.

17. A method as defined in claim 16, wherein said solution and said cellulosic fibrous material are subjected to agitation while in said pulper.

18. A method as defined in claim 10, wherein said antimicrobial agent is present in an amount between about 0.04% to about 1.0% by weight of said antimicrobially-treated cellulosic fibrous material.

19. A method as defined in claim 10, wherein said antimicrobial agent is present in an amount between about 0.2% to about 0.5% by weight of said antimicrobially-treated cellulosic fibrous material.

20. A method as defined in claim 10, wherein said cellulosic fibrous material comprises high-average length pulp fibers, low-average length pulp fibers, or mixtures thereof.

21. A method as defined in claim 10, wherein said nonwoven substrate is formed from continuous filaments.

22. A method as defined in claim 21, wherein said continuous filaments are formed by a spunbond process.

23. A method as defined in claim 10, further comprising drying said web so that said antimicrobial agent forms a covalent bond with said cellulosic fibrous material.

24. A method as defined in claim 23, wherein said antimicrobial agent is an organosilicone compound such that said covalent bond is a siloxane bond.

25. A method as defined in claim 10, wherein greater than about 90% of the cellulosic fibrous material present within said web is derived from said antimicrobially-treated cellulosic fibrous material.

26. A method for forming an antimicrobially-treated fabric, said method comprising:

forming a solution from a liquid and an antimicrobial agent, said antimicrobial agent being an organosilicone quaternary ammonium compound, wherein said organosilicone quaternary ammonium compound has the following structure:

wherein,
$R_1$ is hydrogen or a $C_1$–$C_8$ alkyl group;
$R_2$ is hydrogen or a $C_1$–$C_8$ alkyl group;
$R_3$ and $R_4$ are the same or different, and are selected from the group consisting of hydrogen and a $C_1$–$C_4$ alkyl group;
$R_5$ is hydrogen or a $C_1$–$C_{30}$ alkyl group; and
$X^-$ is a suitable counterion;

combining pulp fibers with said solution to form a liquid suspension while under agitation, wherein said organosilicone quaternary ammonium compound becomes substantive to said pulp fibers after being combined therewith;

forming a web from said liquid suspension of said antimicrobially-treated cellulosic fibrous material such that greater than about 90% of the cellulosic fibrous material present within said web is derived from said antimicrobially-treated cellulosic fibrous material hydraulically entangling said web of antimicrobially-treated pulp fibers with a spunbond nonwoven substrate that contains continuous filaments; and drying said web so that said antimicrobial agent forms a siloxane bond with pulp fibers, wherein said antimicrobially-treated cellulosic fibrous material comprises from about 60% to about 90% by weight of the fabric.

27. A method as defined in claim 26, wherein at least a portion of said liquid from said liquid suspension is removed during formation of said web, said removed liquid portion being substantially free from said antimicrobial agent.

28. A method as defined in claim 26, wherein said antimicrobial agent is 3-(trimethoxysilyl) propyloctadecyldimethyl ammonium chloride.

29. A method as defined in claim 26, wherein said solution and said pulp fibers are combined in a pulper.

30. A method for forming an antimicrobially-treated fabric, said method comprising:

forming a solution from a liquid and an antimicrobial agent;

combining a cellulosic fibrous material with said solution to form a liquid suspension, wherein said antimicrobial agent becomes substantive to said cellulosic fibrous material after being combined therewith, wherein said antimicrobial agent is present in an amount between about 0.04% to about 1.0% by weight of said antimicrobially-treated cellulosic fibrous material;

forming a web from said liquid suspension of said antimicrobially-treated cellulosic fibrous material such that substantially all of the cellulosic fibrous material present within said web is derived from said antimicrobially-treated cellulosic fibrous material; and hydraulically entangling said web of antimicrobially-treated pulp fibers with a nonwoven substrate.

31. A method as defined in claim 30, wherein at least a portion of said liquid from said liquid suspension is removed during formation of said web, said removed liquid portion being substantially free from said antimicrobial agent.

32. A method as defined in claim 30, wherein said antimicrobial agent is an organosilicone quaternary ammonium compound.

33. A method as defined in claim 32, wherein said organosilicone quaternary ammonium compound has the following structure:

wherein,
$R_1$ is hydrogen or a $C_1$–$C_8$ alkyl group;
$R_2$ is hydrogen or a $C_1$–$C_8$ alkyl group;
$R_3$ and $R_4$ are the same or different, and are selected from the group consisting of hydrogen and a $C_1$–$C_4$ alkyl group;
$R_5$ is hydrogen or a $C_1$–$C_{30}$ alkyl group; and
$X^-$ is a suitable counterion.

34. A method as defined in claim 30, wherein said antimicrobial agent is 3-(trimethoxysilyl) propyloctadecyidimethyl ammonium chloride.

35. A method as defined in claim 30, wherein said antimicrobial agent is hydrolyzed prior to forming said solution.

36. A method as defined in claim 30, wherein said solution and said cellulosic fibrous material are combined in a pulper.

37. A method as defined in claim 36, wherein said solution and said cellulosic fibrous material are subjected to agitation while in said pulper.

38. A method as defined in claim 30, wherein said antimicrobial agent is present in an amount between about 0.2% to about 0.5% by weight of said antimicrobially-treated cellulosic fibrous material.

39. A method as defined in claim 30, wherein said cellulosic fibrous material comprises high-average length pulp fibers, low-average length pulp fibers, or mixtures thereof.

40. A method as defined in claim 30, wherein said nonwoven substrate is formed from continuous filaments.

41. A method as defined in claim 40, wherein said continuous filaments are formed by a spunbond process.

42. A method as defined in claim 30, further comprising drying said web so that said antimicrobial agent forms a covalent bond with said cellulosic fibrous material.

43. A method as defined in claim 42, wherein said antimicrobial agent is an organosilicone compound such that said covalent bond is a siloxane bond.

44. A method as defined in claim 30, wherein said antimicrobially-treated cellulosic fibrous material comprises from about 60% to about 90% by weight of the fabric.

45. A method as defined in claim 30, wherein greater than about 90% of the cellulosic fibrous material present within said web is derived from said antimicrobially-treated cellulosic fibrous material.

* * * * *